(12) United States Patent
Bianchini et al.

(10) Patent No.: US 11,203,649 B2
(45) Date of Patent: Dec. 21, 2021

(54) FUNCTIONALIZED HYALURONIC ACID OR A DERIVATIVE THEREOF IN THE TREATMENT OF INFLAMMATORY STATES

(71) Applicant: JOINTHERAPEUTICS S.R.L., Como (IT)

(72) Inventors: Giulio Bianchini, Como (IT); Lanfranco Callegaro, Como (IT)

(73) Assignee: JOINTHERAPEUTICS S.R.L., Como (IT)

( * ) Notice: Subject to any disclaimer, the term of this patent is extended or adjusted under 35 U.S.C. 154(b) by 52 days.

(21) Appl. No.: 16/757,864

(22) PCT Filed: Oct. 24, 2018

(86) PCT No.: PCT/IB2018/058297
§ 371 (c)(1),
(2) Date: Apr. 21, 2020

(87) PCT Pub. No.: WO2019/082097
PCT Pub. Date: May 2, 2019

(65) Prior Publication Data
US 2021/0189017 A1 Jun. 24, 2021

(30) Foreign Application Priority Data

Oct. 26, 2017 (IT) .................. 102017000122135

(51) Int. Cl.
| C08B 37/08 | (2006.01) |
| A61K 31/728 | (2006.01) |
| A61P 37/06 | (2006.01) |
| A61K 45/06 | (2006.01) |

(52) U.S. Cl.
CPC ........ *C08B 37/0072* (2013.01); *A61K 31/728* (2013.01); *A61K 45/06* (2013.01); *A61P 37/06* (2018.01)

(58) Field of Classification Search
None
See application file for complete search history.

(56) References Cited

U.S. PATENT DOCUMENTS

| 4,851,521 A | 7/1989 | Della Valle et al. |
| 6,756,363 B1 * | 6/2004 | Nordquist ............ A61K 31/722 514/55 |
| 2015/0231268 A1 | 8/2015 | Nakai et al. |

FOREIGN PATENT DOCUMENTS

| EP | 0341745 A1 | 11/1989 |
| LU | 91414 A2 | 8/2009 |
| WO | 1998045335 A1 | 10/1998 |
| WO | 2000001733 A1 | 1/2000 |

OTHER PUBLICATIONS

Lee Y-T, et al., "Hyaluronic acid modulates gene expression of connective tissue growth factor (CTGF), transforming growth factor-beta 1 (TGF-beta 1), and vascular endothelial growth factor (VEGF) in human fibroblast-like synovial cells from advanced-stage osteoarthritis in vitro", J. Orthop Res 28:492-496, 2010.
Search Report and Written Opinion of PCT/IB2018/058297 dated Dec. 13, 2018.
Zorzi C., et al., "A new hydrogel for the conservative treatment of meniscal lesions: a randomized controlled study", Joints, 2015; 3(3):136-145.

* cited by examiner

*Primary Examiner* — Dale R Miller
(74) *Attorney, Agent, or Firm* — Silvia Salvadori, P.C.; Silvia Salvadori

(57) ABSTRACT

The present invention discloses a functionalized hyaluronic acid or a derivative thereof, as well as a process for the preparation thereof, and the use thereof as a biomaterial and as an ingredient in pharmaceutical compositions. The present invention furthermore discloses the use of said functionalized hyaluronic acid or a derivative thereof in the treatment of pathologies ascribable to altered galectin expression.

8 Claims, 4 Drawing Sheets

FUNCTIONALIZED HYALURONIC ACID OR A DERIVATIVE THEREOF IN THE TREATMENT OF INFLAMMATORY STATES

This application is a U.S. national stage of PCT/IB2018/058297 filed on 24 Oct. 2018, which claims priority to and the benefit of Italian Application No. 102017000122135 filed on 26 Oct. 2017, the contents of which are incorporated herein by reference in their entireties.

FIELD OF THE INVENTION

The present invention relates to functionalized hyaluronic acid or a derivative thereof, as well as a process for its preparation, and its use as a biomaterial and as an ingredient in pharmaceutical compositions.

BACKGROUND ART

Galectins are a family of proteins which are defined by their binding specificity for 3-galactoside sugars, such as N-acetyl-lactosamine, which can be bound to proteins via N-glycosylation or O-glycosylation. 15 galectins are known in mammals, which are encoded by LGALS genes and are numbered consecutively, but only galectins −1, −2, −3, −4, −7, −8, −9, −10, −12, and −13 have been identified in humans.

These are located at intracellular or extracellular level. In the latter case, they perform bivalent or multivalent interactions with glycans on cell surfaces and induce various cellular responses, including the production of cytokines and other inflammatory mediators, cell adhesion, migration, and apoptosis. Furthermore, they can form lattices with membrane glycoprotein receptors and modulate the properties of the receptors. Intracellular galectins can participate in signalling pathways and alter biological responses, including apoptosis, cell differentiation, and cell motility. Current evidence indicates that galectins play an important role in acute and chronic inflammatory responses, as well as in other different pathological processes.

Recent studies have shown that certain galectins are involved in the inflammatory response of certain musculoskeletal disorders, such as rheumatoid arthritis and osteoarthritis (D. Weinmann et al. Scientific Reports DOI: 10.1038/srep39112; Toegel S. et al Histochem Cell Biol 2014, 142, 373; Toegel S. The Journal of Immunology 2016, 1910; Li S. et al. J. Clin. Cell Immunol 2013, 4(5), 1000164). Galectins are overexpressed in many inflammatory pathologies, therefore the inhibition of metalloproteinase activity can consequently determine a marked reduction in the inflammatory cascade.

Furthermore, it is known that galectins perform an active role in the development and progression of tumours. For this reason, galectin inhibitors/modulators are currently being studied in order to improve both the diagnosis and the treatment of neoplasia. (Ebrahim A H, et al. Galectins in cancer: carcinogenesis, diagnosis and therapy. Ann Transl Med 2014; 2(9):88. doi: 10.3978/j.issn.2305-5839.2014.09.12) An object of the present invention is therefore to provide a product which regulates the expression of these receptors, so as to act therapeutically on pathologies ascribable to altered galectin expression while also offering a high acceptability profile thereof from a medical and a pharmaceutical viewpoint.

SUMMARY OF THE INVENTION

Said object has been achieved by a functionalized hyaluronic acid or a derivative thereof, as stated in Claim 1.

In another aspect, the present invention relates to a process for preparing the functionalized hyaluronic acid or a derivative thereof.

In a further aspect, the present invention relates to the use of said functionalized hyaluronic acid or a derivative thereof in the treatment of pathologies ascribable to altered galectin expression. Non-limiting examples of pathologies affected by over/under regulation of said receptors are non-alcoholic steatohepatitis, plaque psoriasis, rheumatoid arthritis, osteoarthritis, neoplasia, and fibrotic pulmonary, renal, and cardiovascular processes.

In a further aspect, the present invention concerns the use of said functionalized hyaluronic acid or a derivative thereof as a biomaterial or a scaffold for cell growth, in the treatment of orthopaedic diseases.

In an even further aspect, the present invention concerns the use of said functionalized hyaluronic acid or a derivative thereof as a biomaterial or a scaffold for cell growth, in plastic/cosmetic surgery, haemodialysis, cardiology, angiology, ophthalmology, otolaryngology, odontology, gynaecology, urology, dermatology, oncology, and tissue repair.

In an even further aspect, the present invention relates to a pharmaceutical composition comprising at least one functionalized hyaluronic acid or a derivative thereof and at least one pharmacologically active substance and/or at least one bioactive substance.

In an even further aspect, the present invention relates to the use of said pharmaceutical composition in the treatment of pathologies ascribable to altered galectin expression. Non-limiting examples of pathologies affected by over/under regulation of said receptors are non-alcoholic steatohepatitis, plaque psoriasis, rheumatoid arthritis, osteoarthritis, neoplasia, and fibrotic pulmonary, renal, and cardiovascular processes.

In an even further aspect, the present invention concerns the use of said pharmaceutical composition in plastic/cosmetic surgery, haemodialysis, cardiology, angiology, ophthalmology, otolaryngology, odontology, gynaecology, urology, dermatology, oncology, and tissue repair.

BRIEF DESCRIPTION OF THE FIGURES

The characteristics and advantages of the present invention will become apparent from the following detailed description, the embodiments provided by way of non-limiting examples and the figures annexed hereto, wherein.

DETAILED DESCRIPTION OF THE INVENTION

Figure 1:
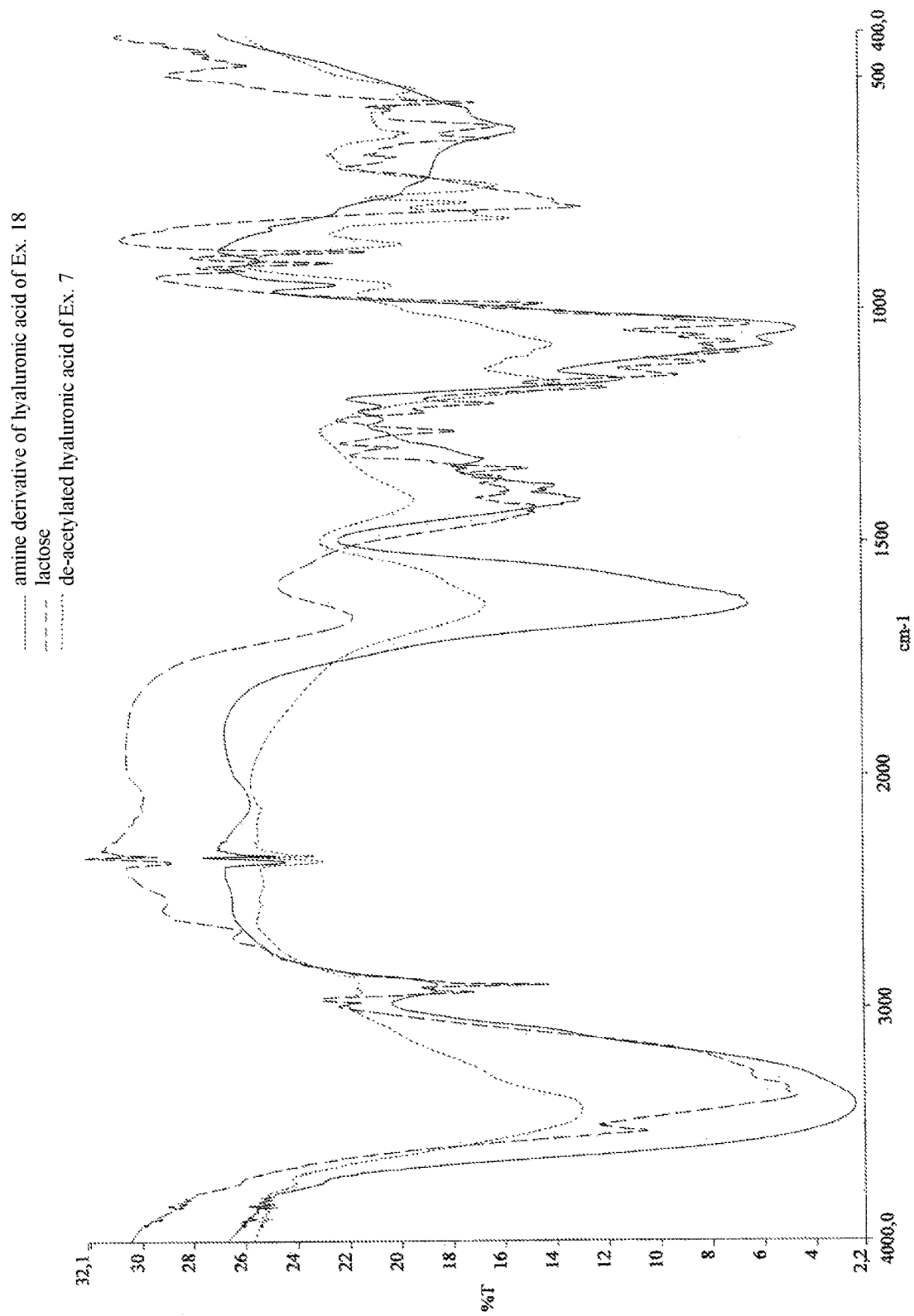
FIG. 1 shows the comparison among the infrared spectra of lactose, deacetylated hyaluronic acid, and a derivative of hyaluronic acid, wherein R5 is Z(3) and Z3 is a galactose moiety.
Figure 2:
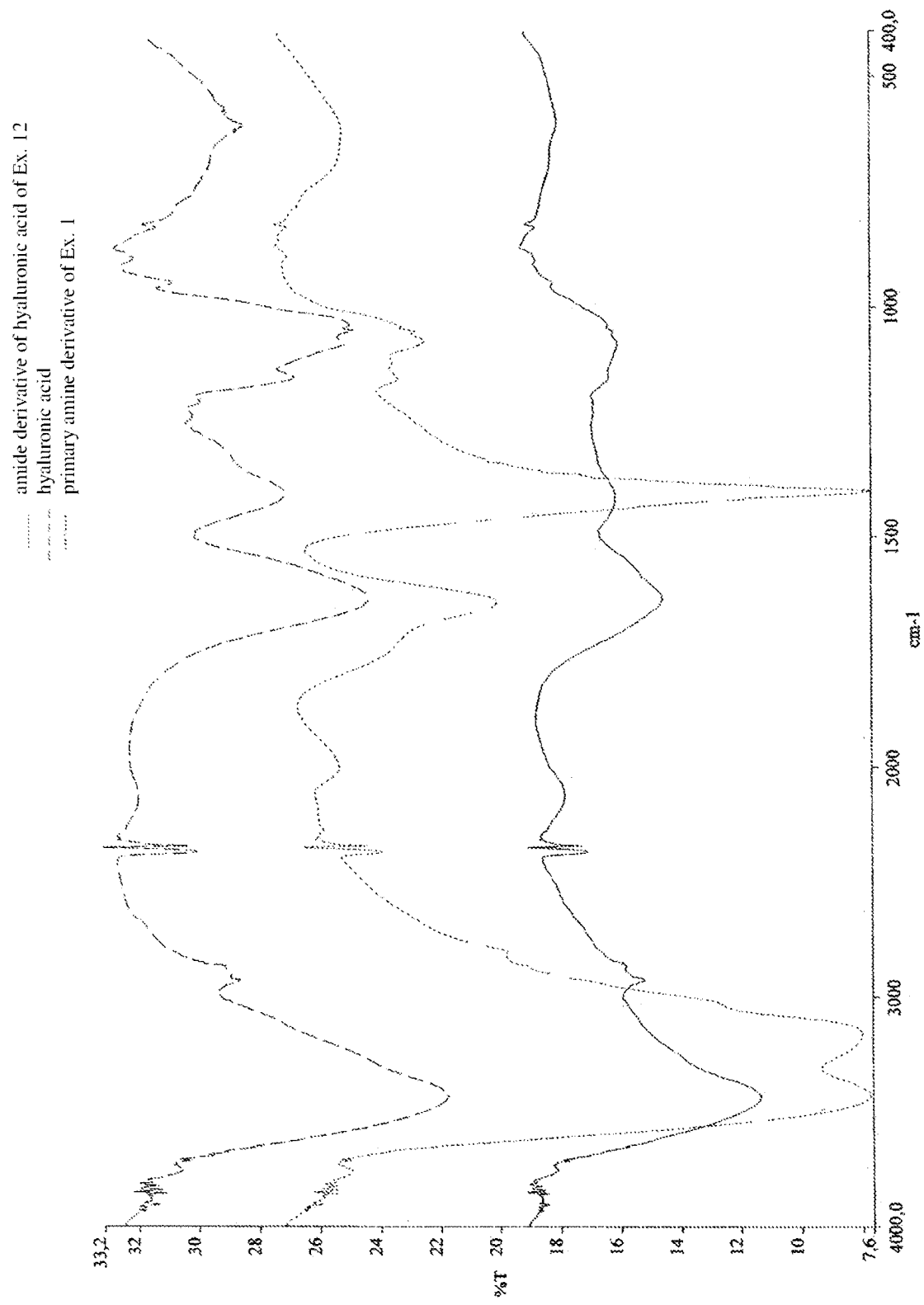
FIG. 2 shows the comparison among the infrared spectra of hyaluronic acid, an amine derivative of the reducing sugar obtained via reductive amination, and a derivative of hyaluronic acid, wherein R is Z(1) and Z3 is a galactose moiety.
Figure 3:
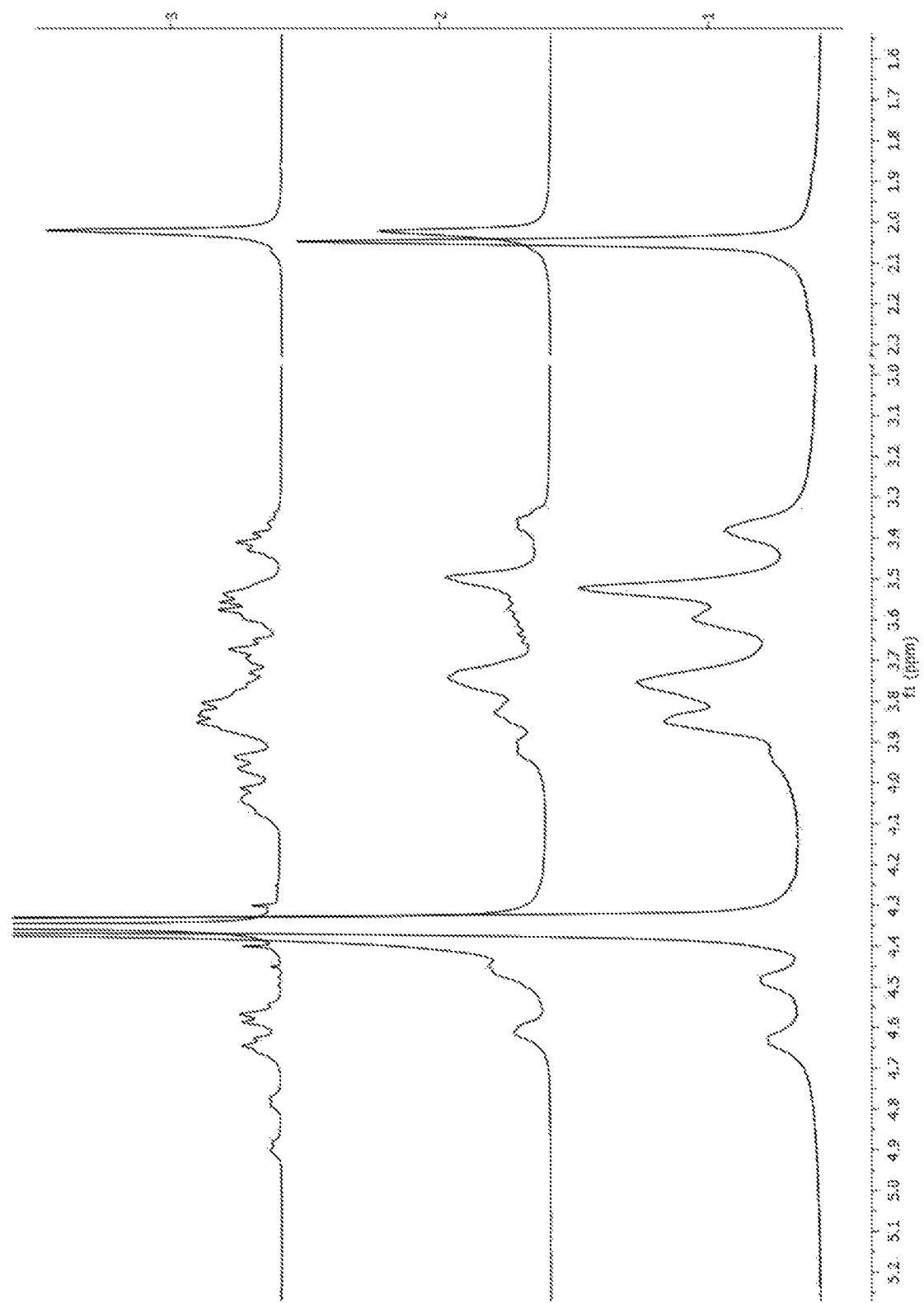
FIG. 3 shows $^1$H-NMR spectra (400 MHz, D$_2$O, 343 K): 1) sodium hyaluronate; 2) sodium hyaluronate obtained according to Example 6; 3) amine derivatives of partially deacetylated hyaluronic acid (reductive amination with reducing sugars) obtained according to Example 13.
Figure 4:
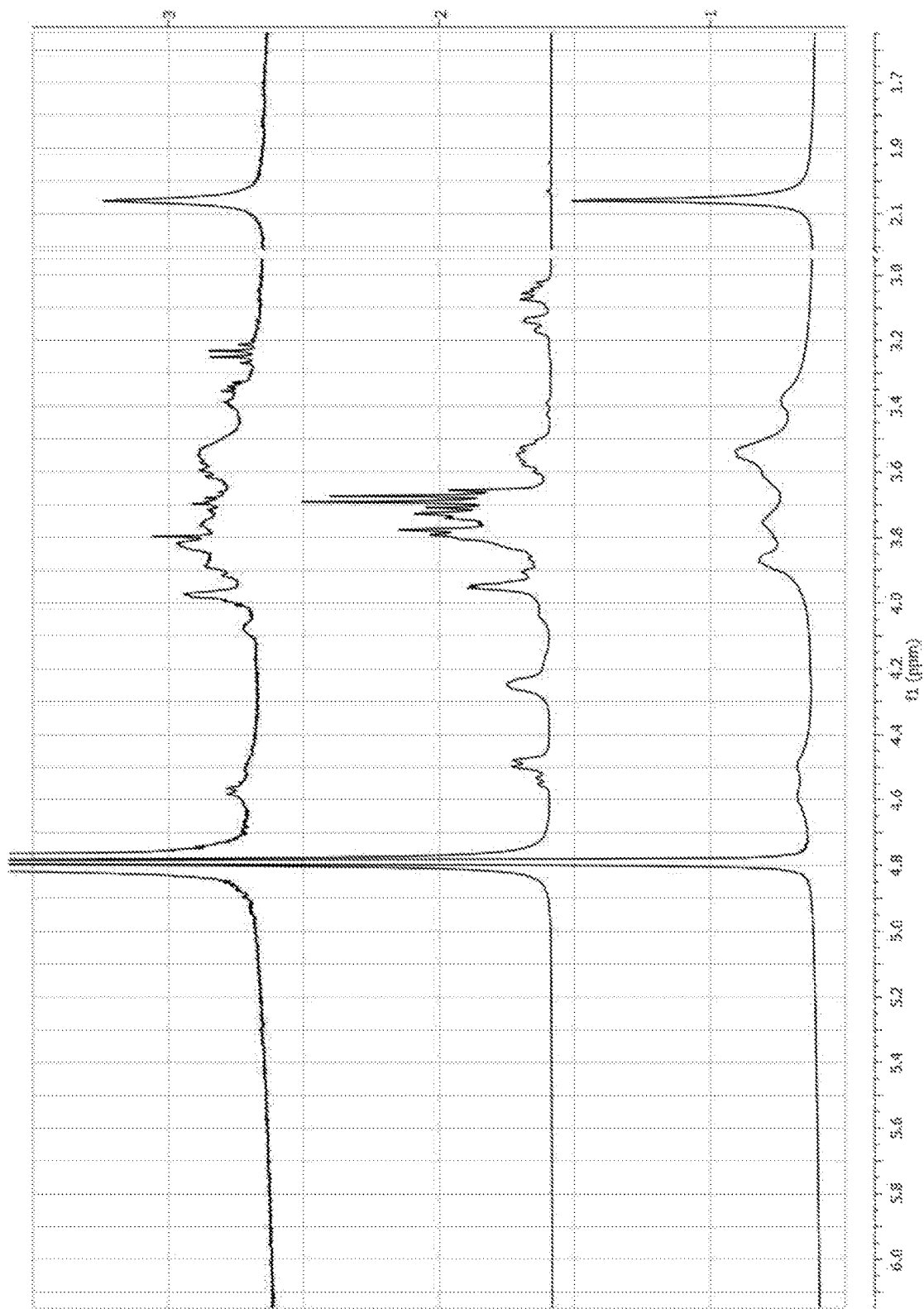
FIG. 4 shows $^1$H-NMR spectra (400 MHz, D$_2$O, 298 K): 1) sodium hyaluronate; 2) amine derivative of a reducing sugar obtained according to Example 3; 3) amide derivative of partially deacetylated hyaluronic acid (amidation with amine derivatives of reducing sugars) obtained according to Example 13.

The invention relates, therefore, to functionalized hyaluronic acid or a derivative thereof having the formula (I):

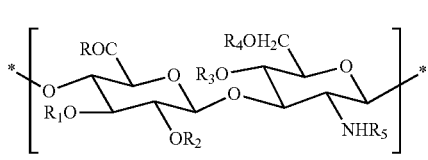

wherein $R_1$, $R_2$, $R_3$, $R_4$ are, independently of one another, H, $SO_3^-$, an acyl group derived from a carboxylic acid of the aliphatic, aromatic, arylaliphatic, cycloaliphatic, heterocyclic series, —CO—$(CH_2)_2$—COOY, where Y is a negative charge or H, and R is Z(1) or Z(2), and $R_5$ is —CO—CH3, H, $SO_3^-$, an acyl group derived from a carboxylic acid of the aliphatic, aromatic, arylaliphatic, cycloaliphatic, heterocyclic series, an acyl group of acid hyaluronic acid, where Z(1) is a moiety of formula (1):

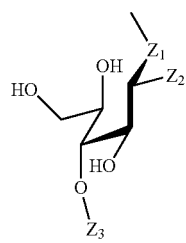

wherein $Z_1$ is —$NR_6CH_2$—, and $R_6$ is H or an aliphatic, aromatic, arylaliphatic, cycloaliphatic, heterocyclic group, substituted or non-substituted, $Z_2$ is —OH, or —$NHCOCH_3$, $Z_3$ is H, monosaccharide, disaccharide, or oligosaccharide, or Z(2) is a moiety of formula (2):

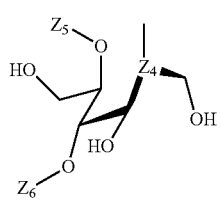

wherein $Z_4$ is —$NR_6CH$—, and $R_6$ is H or an aliphatic, aromatic, arylaliphatic, cycloaliphatic, heterocyclic group, substituted or non-substituted, $Z_5$ and $Z_6$ are, independently of each other, H, monosaccharide, disaccharide, or oligosaccharide, or R5 is Z(3) or Z(4), and R is $NR_6R_7$, or an alcoholic group of the aliphatic, aromatic, arylaliphatic, cycloaliphatic, heterocyclic series, OH, $O^-$, an alcoholic group of hyaluronic acid, an amine group of hyaluronic acid, and $R_6$, $R_7$ are, independently of each other, H or an aliphatic, aromatic, arylaliphatic, cycloaliphatic, heterocyclic group, substituted or non-substituted, where Z(3) is a moiety of formula (3):

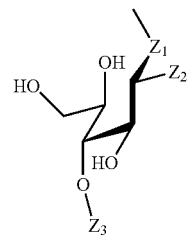

wherein $Z_1$ is —$CH_2$— or —CO—, $Z_2$ is —OH, or —$NHCOCH_3$, $Z_3$ is H, monosaccharide, disaccharide, or oligosaccharide, or Z(4) is a moiety of formula (4):

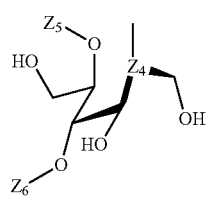

wherein $Z_4$ is —CH—, $Z_5$ and $Z_6$ are, independently of each other, H, monosaccharide, disaccharide, or oligosaccharide, or R is Z(1) or Z(2), and $R_5$ is Z(3) or Z(4).

The term "aliphatic, aromatic, arylaliphatic, cycloaliphatic, heterocyclic" preferably means a linear, branched, or cyclic moiety, saturated or unsaturated, aliphatic or aromatic, selected from: C1-C10 alkyl, substituted C1-C10 alkyl, C2-C10 alkenyl, substituted C2-C10 alkenyl, C4-C10 dienyl, substituted C4-C10 dienyl, C2-C10 alkynyl, substituted C2-C10 alkynyl, phenyl, substituted phenyl, aryl, substituted aryl, heteroaryl, substituted heteroaryl, C1-C10 alkylthio, substituted C1-C10 alkylthio, phenylthio, substituted phenylthio, arylthio, substituted arylthio, carbonyl, substituted C1-C6 carbonyl, carboxyl, substituted C1-C6 carboxyl, amino, substituted C1-C6 amino, amide, substituted C1-C6 amide, sulfonyl, substituted C1-C6 sulfonyl, sulfonic acid, phosphonyl, substituted C1-C6 phosphonyl, polyaryl, substituted polyaryl, C3-C20 cycloalkyl, substituted C3-C20 cycloalkyl, C3-C20 heterocycloalkyl, substituted C3-C20 heterocycloalkyl, C2-C10 cycloalkenyl, substituted C2-C10 cycloalkenyl, C4-C10 cyclodienyl, substituted C4-C10 cyclodienyl, or amino acid. The term "substituted" means bound to at least one halogen, hydroxyl, C1-C4 alkyl, carboxyl, or combinations thereof.

Preferably, $Z_3$, $Z_5$ e $Z_6$ are, independently of one another, H, moiety of glucose, galactose, arabinose, xylose, mannose, lactose, trehalose, gentiobiose, cellobiose, cellotriose, maltose, maltotriose, chitobiose, chitotriose, mannobiose, melibiose, fructose, N-acetyl glucosamine, N-acetylgalactosamine, or a combination thereof.

More preferably, $Z_3$ is H, moiety of glucose, galactose, mannose, N-acetylglucosamine, N-acetylgalactosamine, or a combination thereof.

In particularly preferred embodiments, the moiety of formula Z is a moiety of lactose or galactose, wherein Z is any one of Z(1), Z(2), Z(3) and Z(4).

As can be seen from the structure formula shown above, hyaluronic acid or a derivative thereof is functionalized through conjugation with a moiety of formula Z, whether Z(1), Z(2), Z(3) or Z(4), by:

1) an amide bond between the carboxylic group of hyaluronic acid or a derivative thereof and an amine, via reductive amination of the precursor of Z with primary amines or ammonia sources, 2) an amine bond between the amine group of hyaluronic acid or a derivative thereof, having been previously deacetylated, and the moiety Z, via reductive amination, 3) an amide bond between the amine group of hyaluronic acid or a derivative thereof, having been previously deacetylated, and carboxyl group of the precursor of the moiety Z.

Therefore, in another aspect, the present invention relates to a process for preparing the functionalized hyaluronic acid or a derivative thereof, said process comprising the following steps:

i) providing hyaluronic acid or a partially or totally deacetylated derivative thereof;

ii) providing an amine derivative of a monosaccharide, disaccharide, oligosaccharide through a reductive amination reaction;

iii) reacting:
a) said hyaluronic acid of step i) with the amine derivative of step ii) in the presence of carbodiimides and/or in the presence of carboxy group activators,
or
b) said partially or totally deacetylated derivative of step i) with a monosaccharide, disaccharide, oligosaccharide in the presence of an amino-borane;
or
c) partially or totally deacetylated derivative of step i) with a carboxylic derivative of monosaccharide, disaccharide, oligosaccharide in the presence of carbodiimides and/or in the presence of carboxy group activators;
or
d) the derivative obtained from step iii-b) with the amine derivative of step ii) in the presence of carbodiimides and/or in the presence of carboxy group activators;
or
e) the derivative obtained from step iii-c) with the amine derivative of step ii) in the presence of carbodiimides and/or in the presence of carboxy group activators;
and iv) precipitating the functionalized hyaluronic acid or a derivative thereof so obtained with an organic solvent.

It has surprisingly been observed that the amino-boranes show a marked selectivity in the reduction of the imino group compared with the carbonyl group and are compatible with the aqueous medium, thereby allowing effective amine reduction of reducing sugars in the presence of primary amines, ammonia sources, and amine moieties of polysaccharides. At the same time, the presence of carbodiimides and/or carboxylic group activators effectively promotes the formation of amide derivatives of hyaluronic acid with excellent selectivity with respect to the formation of ester derivatives. Therefore, the process as a whole advantageously offers the possibility of combining monosaccharides, disaccharides, and oligosaccharides to the hyaluronic acid main chain without needing the introduction of chemical spacers.

The derivatives of hyaluronic acid which can be used in the preparation of functionalized derivatives according to the present invention are preferably as follows:

hyaluronic acid salts, such as sodium hyaluronate, potassium hyaluronate, calcium hyaluronate, magnesium hyaluronate, zinc hyaluronate, cobalt hyaluronate, ammonia hyaluronate, tetrabutylammonium hyaluronate, and mixtures thereof, hyaluronic acid esters, wherein a part or all of the carboxylic groups are esterified with aliphatic, aromatic, arylaliphatic, cycloaliphatic, or heterocyclic series alcohols, as also described in EP0216453B1, self-cross-linked hyaluronic acid esters, wherein a part or all of the carboxylic groups are esterified with alcoholic groups from the same polysaccharide chain or other chains, as also described in EP0341745B1, cross-linked hyaluronic acid compounds, wherein a part or all of the carboxylic groups are esterified with aliphatic, aromatic, arylaliphatic, cycloaliphatic, or heterocyclic series polyalcohols, generating cross-linking by spacer chains, as also described in EP0265116B1, succinic acid hemiester or succinic acid heavy metal salts with hyaluronic acid or with partial or total hyaluronic acid esters, as also described in WO96/357207, O-sulfated derivatives, as also described in WO95/25751, or N-sulfated derivatives, as also described WO1998/045335.

Said monosaccharide, disaccharide, or oligosaccharide corresponds to the definition given above for the moiety Z.

Said amino-borane is preferably 2-methylpyridine borane, 5-ethyl-2-methylpyridine borane, pyridine borane, trimethylamine borane, triethylamine borane, dimethylamine borane, tert-butylamine borane, or a mixture thereof. More preferably, said amino-borane is 2-methylpyridine borane, 5-ethyl-2-methylpyridine borane, or a mixture thereof.

The amino-boranes may be used as such or may be previously solubilised or dispersed in water-miscible organic solvents such as alcohols. The most preferred among said alcohols are methanol, ethanol, 2-propanol, or a mixture thereof.

The term "organic solvent" means an organic water-miscible solvent capable of lowering the dielectric constant of the aqueous reaction solution. Suitable organic solvents are acetone, methanol, ethanol, 2-propanol, or a mixture thereof, and preferably the organic solvent is ethanol or 2-propanol or a mixture thereof.

The term "carboxyl group activator" means those reagents which modify the hydroxyl function of said group, thus promoting its elimination in the substitution reactions. Activators of the carboxylic group include hydroxybenzotriazole, 1,1'-carbodiimidazole, p-nitrophenol, N-hydroxysulfosuccinimide sodium salt, N-hydroxysuccinimide, and mixtures thereof.

Suitable carbodiimides include dicyclohexylcarbodiimide, 1-ethyl-3-(3-dimethylamino-propyl) carbodiimide hydrochloride, 1-ethyl-3-(3-dimethylamino-propyl) carbodiimide, N,N'-diisopropylcarbodiimide and mixtures thereof.

Optionally, the precipitate separated in step iv) is washed with mixtures of water and organic solvent, with water in percentages of up to 30%, and more preferably up to 10%.

Preferably, in step iii), the molar ratio of monosaccharide, disaccharide, or oligosaccharide to hyaluronic acid or a derivative thereof is 0.5 to 30, more preferably 1 to 20, even more preferably 1 to 10.

In a further aspect, the present invention relates to the use of said functionalized hyaluronic acid or a derivative thereof in the treatment of pathologies ascribable to altered galectin expression. Non-limiting examples of pathologies affected by over/under regulation of said receptors are non-alcoholic steatohepatitis, plaque psoriasis, rheumatoid arthritis, osteoarthritis, neoplasia, and fibrotic pulmonary, renal, and cardiovascular processes.

Examples of neoplasia and fibrotic processes include acute lymphoblastic leukaemia, idiopathic pulmonary fibrosis, hepatic fibrosis, cardiac fibrosis, renal fibrosis, and ovarian, prostate, lung, stomach, skin, thyroid, and pancreas tumours.

In a further aspect, the present invention concerns the use of said functionalized hyaluronic acid or a derivative thereof as a biomaterial or a scaffold for cell growth, in the treatment of orthopaedic diseases.

In an even further aspect, the present invention concerns the use of said functionalized hyaluronic acid or a derivative thereof as a biomaterial or a scaffold for cell growth, in plastic/cosmetic surgery, haemodialysis, cardiology, angiology, ophthalmology, otolaryngology, odontology, gynaecology, urology, dermatology, oncology, and tissue repair.

Functionalized hyaluronic acid or a derivative thereof can also be used as a biomaterial for coating objects used in the medical field and in other sectors of industry, providing the surface of the object used as a medium with new biological characteristics.

Objects which can be coated include, for example, catheters, tubes, probes, cardiac valves, soft tissue prostheses, prostheses of animal origin, artificial tendons, bone and cardiovascular prostheses, contact lenses, blood oxygenators, artificial kidneys, heart, pancreas, liver, blood bags, syringes, surgical instruments, filtration systems, laboratory instruments, containers, for cultures and for the regeneration of cells and tissues, media for peptides, proteins, and antibodies.

Functionalized hyaluronic acid or a derivative thereof can also be used in the cosmetic field and in dermatology.

In an even further aspect, the present invention relates to a pharmaceutical composition comprising at least one functionalized hyaluronic acid or a derivative thereof and at least one pharmacologically active substance and/or at least one bioactive substance.

Suitable pharmacologically active substances include antibiotics, anti-infectives, antimicrobials, antivirals, cytostatics, cytotoxics, anti-tumour drugs, anti-inflammatory drugs, cicatrizants, anaesthetics, analgesics, vasoconstrictors, cholinergic or adrenergic agonists and antagonists, antithrombotics, anticoagulants, haemostatics, fibrinolytics, thrombolytics, proteins and fragments thereof, peptides, polynucleotides, growth factors, enzymes, vaccines, or combinations thereof.

Preferably, said bioactive substance is selected from collagen, fibrinogen, fibrin, alginic acid, sodium alginate, potassium alginate, magnesium alginate, cellulose, chondroitin sulfate, dermatan sulfate, keratan sulfate, heparin, heparan sulfate, laminin, fibronectin, elastin, polylactic acid, polyglycolic acid, poly(lactic-co-glycolic acid), polycaprolactone, gelatin, albumin, poly(glycolide-co-caprolactone), poly(glycolide-co-trimethylene carbonate), hydroxyapatite, tricalcium phosphate, dicalcium phosphate, demineralized bone matrix, and mixtures thereof.

Preferably, said at least one functionalized hyaluronic acid or a derivative thereof and said at least one bioactive substance are in a ratio by weight of from 100:1 to 1:150.

In an even further aspect, the present invention relates to the use of said pharmaceutical composition in the treatment of pathologies ascribable to altered galectin expression.

Non-limiting examples of pathologies affected by over/under regulation of said receptors are non-alcoholic steatohepatitis, plaque psoriasis, rheumatoid arthritis, osteoarthritis, neoplasia, and fibrotic pulmonary, renal, and cardiovascular processes.

In an even further aspect, the present invention concerns the use of said pharmaceutical composition in plastic/cosmetic surgery, haemodialysis, cardiology, angiology, ophthalmology, otolaryngology, odontology, gynaecology, urology, oncology, dermatology, and tissue repair.

Preferably, the pharmaceutical composition according to the invention comprises up to 10 wt % of said at least one functionalized hyaluronic acid or a derivative thereof, based on the weight of the pharmaceutical composition, and more preferably, up to 5 wt % of said at least one functionalized hyaluronic acid or a derivative thereof. Particularly preferable are pharmaceutical compositions wherein the amount of said at least one functionalized hyaluronic acid or a derivative thereof is 0.5-5 wt %, based on the weight of the pharmaceutical composition.

In particularly preferred embodiments, the present invention relates to a pharmaceutical composition comprising at least one functionalized hyaluronic acid or a derivative thereof, as described above, and hydroxyapatite, tricalcium phosphate or mixtures thereof. Said compositions find advantageous use in orthopaedic applications concerning the skeletal system.

The pharmaceutical composition may be administered orally, intramuscularly, intravenously, intra-articularly, transdermally, subdermally, or topically externally or internally, for example by surgical means.

Preferably, said pharmaceutical composition is administered intra-articularly, transdermally, or topically internally.

The pharmaceutical composition may further comprise pharmaceutically acceptable excipients.

Suitable pharmaceutically acceptable excipients include, for example, pH regulators, isotonic regulators, solvents, stabilisers, chelating agents, diluents, binders, disintegrators, lubricants, glidants, colorants, suspending agents, surfactants, cryoprotectants, preservatives, and antioxidants.

The present invention also relates to a biomaterial comprising the functionalized hyaluronic acid or a derivative thereof, as described above, either alone or in combination with at least one of the pharmacologically active and/or bioactive substances described above. Said biomaterial may be in the form of microspheres, nanospheres, membranes, sponge, wire, film, gauze, guide ways, tampons, gels, hydrogels, fabrics, non-woven fabrics, cannulas, or a combination thereof.

It should also be understood that all aspects identified as favourable and advantageous for the functionalized hyaluronic acid or a derivative thereof should be deemed equally preferable and advantageous also for the preparation process, the compositions, the biomaterials, and the uses stated above.

It should furthermore be understood that all the possible combinations of the preferred aspects of the functionalized hyaluronic acid or a derivative thereof, the preparation process, the compositions, the biomaterials, and the uses disclosed above are likewise preferred.

Below are working examples of the present invention provided for illustrative purposes.

EXAMPLES

Example 1. Synthesis of Primary Amine Derivatives of Reducing Sugars (4-O-β-D-galactopyranosyl 1-amino-1-deoxy-D-glucitol hydrochloride salt) A solution of lactose (6.25% w/v) and ammonium acetate (56% w/v) in methanol was treated under stirring at room temperature with an amount of 5-ethyl-2-methylpyridine borane complex which is equimolar with respect to lactose. The mixture thus obtained was kept under the same conditions for 16 hours, then the raw reaction product was admixed with an equal volume of isopropanol and subsequently acidified to pH 2-3 with 6N hydrochloric acid, causing precipitation of the hydrochloride salt of the amine derivative of lactose. The precipitate was then isolated and washed with mixtures of ethanol:water (9:1, 3×), ethanol:sodium hydroxide 6N (95:5) to a pH equal to 9, again with ethanol:water (9:1, 2×), and finally with ethanol (1×). The solid thus obtained was then dried under reduced pressure and used for subsequent synthesis steps without further purification. The derivative was characterized by IR spectroscopy. Reaction yield: 90%.

Example 2. Synthesis of Benzylamine Derivatives of Reducing Sugars

A solution of lactose (3% w/v), benzylamine (5% w/v) and 5-ethyl-2-methylpyridine borane (6% w/v) in water and methanol (3:1) was stirred at a temperature of 55° C. and left to react for 20 hours. Subsequently, the mixture was cooled, extracted with dichloromethane and, finally, the aqueous phase evaporated at low pressure obtaining a crystalline white solid which was then washed with ethyl ether and finally recovered by decantation and dried under reduced pressure. The product was characterized by IR and $^1$H-NMR spectroscopy. Reaction yield: 90%.

Example 3. Synthesis of Primary Amine Derivatives of Reducing Sugars

A solution of the derivative obtained according to Example 2 (4% w/v) in methanol and water (1:1) was placed under magnetic stirring at room temperature. Subsequently, Pd on coal (0.4% w/v) was added and the system thus produced was pressurised with hydrogen. After 48 hours, the system was depressurised, admixed with an equi-volume of water, the decanted solid and the solution filtered on celite. The solution thus obtained was dried under reduced pressure, providing a white solid. The product thus obtained was characterized by IR and $^1$H-NMR spectroscopy. Reaction yield: 96%.

Example 4. Synthesis of an Acylating Solution Based on Imidazole Amide of Lactobionic Acid A solution of lactobionic acid (10% w/v) in dimethyl sulfoxide was admixed with 1,1-carbodiimidazole (1 eq.) and stirred at room temperature for 2 hours. The solution thus obtained was subsequently used without further purification.

Example 5. Synthesis of Partially Deacetylated Hyaluronate Sodium (48 h)

A hydrazine sulphate solution (1% w/v) in hydrazine monohydrate was admixed with hyaluronate sodium (2% w/v) and the system thus obtained heated to 55° C. and left to react under stirring for 48 hours. Subsequently, the raw reaction product was cooled, then precipitated with ethanol, then isolated and washed with ethanol and subsequently dried for 24 hours under reduced pressure. After which, the product thus obtained (5% w/v) was dissolved in an aqueous solution of acetic acid (5% v/v), the solution was cooled to 4° C. and an aqueous solution of $HIO_3$ (0.5 M, 60% v/v) was added drop by drop. The mixture was left to react under the same conditions for 1 h and then added with a solution of hydroiodic acid (57% w/v, 11% v/v with respect to the solution) and the system left to react for a further 15 minutes. The solution was then extracted with ethyl ether until complete discoloration, the pH of the aqueous phase was corrected to 7-7.5 with NaOH (1N, 0.1N) and, finally, the product was precipitated with ethanol, washed with ethanol, and dried. The product was characterized by $^1$H-NMR and IR spectroscopy. Reaction yield: 83%, deacetylation degree: 11%.

Example 6. Synthesis of Partially Deacetylated Hyaluronate Sodium (72 h)

A solution of sodium hyaluronate (2% w/v) and hydrazine sulfate (1% w/v) in hydrazine hydrate was placed under magnetic stirring at a temperature of 55° C. for 72 hours. At the end of the reaction time, ethanol was added to precipitate the polymer, the solid obtained was then washed with further ethanol and dried under nitrogen flow. The product was redissolved in a solution of aqueous acetic acid (6% w/v, 5% acetic acid), thermostated at 0-5° C. and admixed with a volume (0.8 eq. by volume) of iodic acid solution in water (7.5% w/v). The system thus obtained was left under stirring for 1 hour, then admixed with a volume (0.11 eq. by volume) of aqueous hydroiodic acid (57%) and left to react for a further 15 minutes. Subsequently, the pH was adjusted to 9 through the addition of an aqueous solution of NaOH 1M and the solution was extracted with ethyl ether until complete discoloration. After which, the product was precipitated with ethanol, washed with ethanol, dried under reduced pressure, and characterized by IR and $^1$H-NMR spectroscopy. Reaction yield: 86%, deacetylation degree: 20%.

Example 7. Synthesis of Partially Deacetylated Hyaluronate Sodium (96 h)

A hydrazine sulphate solution (1% w/v) in hydrazine monohydrate was admixed with hyaluronate sodium (2% w/v) and the system thus obtained heated to 55° C. and left to react under stirring for 96 hours. Subsequently, the raw reaction product was cooled, then precipitated with ethanol, then isolated and washed with ethanol and subsequently dried for 24 hours under reduced pressure. After which, the product thus obtained (5% w/v) was dissolved in an aqueous solution of acetic acid (5% v/v), the solution was cooled to 4° C. and an aqueous solution of $HIO_3$ (0.5 M, 60% v/v) was added drop by drop. The mixture was left to react under the same conditions for 1 h and then added with a solution of hydroiodic acid (57% w/v, 11% v/v with respect to the solution) and the system left to react for a further 15 minutes. The solution was then extracted with ethyl ether until complete discoloration, the pH of the aqueous phase was corrected to 7-7.5 with NaOH (1N, 0.1N) and, finally, the product was precipitated with ethanol, washed with ethanol, and dried. The product was characterized by $^1$H-NMR and IR spectroscopy. Reaction yield: 86%, deacetylation degree: 21%.

Example 8. Synthesis of Partially Deacetylated Hyaluronate Sodium (120 h)

A hydrazine sulphate solution (1% w/v) in hydrazine monohydrate was admixed with hyaluronate sodium (2% w/v) and the system thus obtained heated to 55° C. and left to react under stirring for 120 hours. Subsequently, the raw reaction product was cooled, then precipitated with ethanol, then isolated and washed with ethanol and subsequently dried for 24 hours under reduced pressure. After which, the product thus obtained (5% w/v) was dissolved in an aqueous solution of acetic acid (5% v/v), the solution was cooled to 4° C. and an aqueous solution of $HIO_3$ (0.5 M, 60% v/v) was added drop by drop. The mixture was left to react under the same conditions for 1 h and then added with a solution of hydroiodic acid (57% w/v, 11% v/v with respect to the solution) and the system left to react for a further 15 minutes. The solution was then extracted with ethyl ether until complete discoloration, the pH of the aqueous phase was corrected to 7-7.5 with NaOH (1N, 0.1N) and, finally, the product was precipitated with ethanol, washed with ethanol, and dried. The product was characterized by $^1$H-NMR and IR spectroscopy. Reaction yield: 89%, deacetylation degree: 26%.

Example 9. Synthesis of Partially Deacetylated Hyaluronate Sodium (24 h)

A solution of sodium hyaluronate (2% w/v) and ammonium iodide (0.7% w/v) in hydrazine hydrate was placed under magnetic stirring at a temperature of 60° C. for 24 hours. At the end of the reaction time, ethanol was added to precipitate the polymer and the solid obtained was then washed with ethanol and dried under nitrogen flow. The product was redissolved in a solution of aqueous acetic acid (6% w/v, 5% acetic acid), thermostated at 0-5° C. and admixed with a volume (0.8 eq. by volume) of iodic acid solution in water (7.5% w/v). The system thus obtained was left under stirring for 1 hour, then admixed with a volume (0.11 eq. by volume) of aqueous hydroiodic acid (57%) and left to react for a further 15 minutes. Subsequently, the pH was adjusted to 9 through the addition of an aqueous solution of NaOH 1 M and the solution was extracted with ethyl ether until complete discoloration. After which, the product was precipitated with ethanol, washed with ethanol, and dried under reduced pressure. The solid thus obtained was characterized by IR and $^1$H-NMR spectroscopy. Reaction yield: 88%, deacetylation degree: 15%.

Example 10. Preparation of the Hyaluronic Acid Salt with Tetrabutylammonium

An aqueous solution of sodium hyaluronate (1.6% w/v) was percolated through a column filled with a sulphonic resin in the form of tetrabutylammonium salt (50% V/V with respect to the solution) which had been previously activated with a tetrabutylammonium solution (40% w/v). The eluted solution was then lyophilized.

Example 11. Preparation of the Partially Deacetylated Hyaluronic Acid Salt with Tetrabutylammonium An aqueous solution of partially deacetylated sodium hyaluronate (1.6% w/v) was percolated through a column filled with a sulphonic resin in the form of tetrabutylammonium salt (50% v/v with respect to the solution) which had been previously activated with a tetrabutylammonium solution (40% w/v). The eluted solution was then lyophilized.

Example 12. Amide Derivatives of Hyaluronic Acid (Amidation with Amine Derivatives of Reducing Sugars)

A solution of sodium hyaluronate (0.25% w/v) in water was admixed with the amine derivative obtained in Example 1 (30 eq.) and the resulting solution pH was adjusted to a 6.8 through appropriate addition of sodium hydroxide (1N, 0.1N) or hydrochloric acid (1N, 0.1N). Subsequently, a solution of (3-dimethylaminopropyl)-N'-ethylcarbodiimide hydrochloride (5 eq., 11% w/v) and hydroxybenzotriazole (3.5 eq., 6% w/v) which had been previously solubilized in water:dimethyl sulfoxide (1.1:1) was added drop by drop. The pH of the solution was adjusted to 6.8 through appropriate addition of sodium hydroxide (1N, 0.1N) and the resulting raw product was left to react at room temperature for 16 hours. Subsequently, the pH was appropriately adjusted to 7 with sodium hydroxide/hydrochloric acid (0.1N) and the resulting solution was dialyzed repeatedly (cutoff: 12-14000) against water. After which, the solution was admixed with sodium chloride until a 5% w/v titer was reached and the desired product precipitated with ethanol, dried and characterized by IR and $^1$H-NMR spectroscopy. Reaction yield: 88%, amidation with amine derivative of the reducing sugar: 88%.

Example 13. Amide Derivatives of Hyaluronic Acid (Amidation with Amine Derivatives of Reducing Sugars)

An aqueous solution containing sodium hyaluronate (3% w/v), hydroxybenzotriazole (0.4% w/v), N-ethyl-N-(3-dimethylaminopropyl)carbodiimide hydrochloride (0.6% w/v) and the amine derivative of lactose obtained according to Example 3 (2% w/v) was left under stirring for 22 hours, maintaining the pH at 6.8 through the addition of aqueous solutions of NaOH 0.1 M or of HCl 0.1 M. Subsequently NaCl (5 g/100 mL) was added and the product precipitated with methanol. The solid thus obtained was recovered by decantation, washed with methanol and water (4:1), neat methanol, and finally dried under reduced pressure. The product was characterized by IR and $^1$H-NMR spectroscopy. Reaction yield: 86%, amidation with amine derivative of the reducing sugar: 27%.

Example 14. Amide Derivatives of Hyaluronic Acid (Amidation with Amine Derivatives of Reducing Sugars)

A solution of water and dioxane (1:1), containing sodium hyaluronate (0.5% w/v), N-hydroxysuccinimide (1.3% w/v), N-ethyl-N-(3-dimethylaminopropyl) carbodiimide hydrochloride (1.0% w/v), and the amine derivative of lactose obtained in Example 3 (2.1% w/v), was stirred at room temperature for 12 hours. At the end of the reaction time, sodium hydrogen carbonate was added, adjusting the pH to approximately 9-10 and the solution was left under stirring for a further 3 hours. The pH of the mixture was adjusted to 7 through the addition of acetic acid (50%, v/v), and subsequently sodium chloride (5 g/100 mL) was added and the product then precipitated with ethanol, washed with ethanol and with ether, and finally dried under reduced pressure. The product was characterized by IR and H-NMR spectroscopy. Reaction yield: 85%, amidation with amine derivative of the reducing sugar: 21%.

Example 15. Amide Derivatives of Hyaluronic Acid (Amidation with Amine Derivatives of Reducing Sugars) in Organic Medium A solution of hyaluronic acid tetrabutylammonium salt of (2% w/v) in dimethyl sulfoxide was treated with aqueous hydrochloric acid for pH adjustment to 3 and successively admixed with 1,1-carbonyldiimidazole (1.5 eq.) and left to react for 12 hours. Subsequently, the solution was filtered with a Gooch crucible to remove the solid moiety, the amine derivative obtained in Example 1 (2 eq.) was added and the mixture thus obtained was left to react for 48 hours. After which, a saturated sodium chloride solution was added in a sufficient amount to obtain a final titer of 5% w/v in sodium chloride, the mixture was left under stirring for 1 hour, and finally the product precipitated by the addition of acetone and the solid obtained was isolated and then dried. The product was characterized by IR and $^1$H-NMR spectroscopy. Reaction yield: 80%, amidation with amine derivative of the reducing sugar: 10%.

Example 16. Amide Derivatives of Hyaluronic Acid (Amidation with Amine Derivatives of Reducing Sugars) in Organic Medium A solution of sodium hyaluronate (2% w/v) in dimethylformamide was admixed with 1,1-carbonyldiimidazole (1 eq.). The solution thus obtained was left to react for 6 hours, after which the amine derivative obtained in Example 1 (5 eq.) was added and the system was left to react for a further 36 hours. Subsequently, the product was precipitated with acetone, then isolated, washed with acetone, and subsequently dried under reduced pressure. The product was characterized by IR and $^1$H-NMR spectroscopy. Reaction yield: 80%, amidation with amine derivative of the reducing sugar: 57%.

Example 17. Amine Derivatives of Partially Deacetylated Hyaluronic Acid (Reductive Amination with Reducing Sugars)

An aqueous solution of partially deacetylated sodium hyaluronate obtained according to Example 7 (1.5% w/v) was admixed with lactose (10 eq.) and the pH adjusted with acetic acid (100%) to reach values in the vicinity of 5.5. The system thus obtained was heated to 60° C. and then admixed with a 2-methylpyridine borane solution (10 eq., 10% w/v) in methanol and left to react for 2 hours under the same conditions. Subsequently, the pH of the solution was adjusted with aqueous hydrochloric acid (4N) to values in the vicinity of 2-3 and the system was maintained under the same conditions for 15 minutes. After which the system was cooled, the pH adjusted to 7-7.5 with NaOH (1N) and the resulting solution dialyzed repeatedly (cutoff: 12-14000) against water. Finally, the solution was admixed with sodium chloride until a 5% w/v titer was reached and the desired product precipitated with ethanol, dried and characterized by IR and $^1$H-NMR spectroscopy. Reaction yield: 80%, amination with reducing sugar: 21%.

Example 18. Amine Derivatives of Partially Deacetylated Hyaluronic Acid (Reductive Amination with Reducing Sugars)

An aqueous solution of partially deacetylated sodium hyaluronate obtained according to Example 7 (1.5% w/v) was admixed with lactose (10 eq.) and the pH adjusted with acetic acid (100%) to reach values in the vicinity of 5.5. The system thus obtained was heated to 60° C. and then admixed with a 2-methylpyridine borane solution (10 eq., 10% w/v) in methanol and left to react for 2 hours under the same conditions. Subsequently, the pH of the solution was adjusted with aqueous hydrochloric acid (4N) to values in the vicinity of 2-3 and the system was maintained under the same conditions for 15 minutes. After which, the system was cooled, the pH adjusted to 7-7.5 with NaOH (1N) and sodium chloride was added to reach a titer thereof of 5% w/v. The desired product was then precipitated with ethanol, dried, and characterized by IR and $^1$H-NMR spectroscopy. Reaction yield: 84%, amination with reducing sugar: 21%.

Example 19. Amine Derivatives of Partially Deacetylated Hyaluronic Acid (Reductive Amination with Reducing Sugars)

An aqueous solution of partially deacetylated sodium hyaluronate obtained according to Example 5 (1.5% w/v) was admixed with lactose (10 eq.) and the pH adjusted with acetic acid (100%) to reach values in the vicinity of 5.5. The system thus obtained was heated to 60° C. and then admixed with a 2-methylpyridine borane solution (10 eq., 10% w/v) in methanol and left to react for 2 hours under the same conditions. Subsequently, the pH of the solution was adjusted with aqueous hydrochloric acid (4N) to values in the vicinity of 2-3 and the system was maintained under the same conditions for 15 minutes. After which the system was cooled, the pH adjusted to 7-7.5 with NaOH (1N) and the resulting solution dialyzed repeatedly (cutoff: 12-14000) against water. Finally, the solution was admixed with sodium chloride until a 5% w/v titer was reached and the desired product precipitated with ethanol, dried and characterized by IR and $^1$H-NMR spectroscopy. Reaction yield: 78%, amination with reducing sugar: 11%.

Example 20. Amine Derivatives of Partially Deacetylated Hyaluronic Acid (Reductive Amination with Reducing Sugars)

An aqueous solution of partially deacetylated sodium hyaluronate obtained according to Example 6 (2% w/v) was admixed with lactose (3 eq.) and the pH adjusted with acetic acid (100%) to reach values in the vicinity of 5.5. The system thus obtained was heated to 60° C. and then admixed with a 2-methylpyridine borane solution (1 eq., 10% w/v) in isopropanol and left to react for 3 hours under the same conditions. Subsequently the pH of the reaction was adjusted with aqueous hydrochloric acid (4N) to reach values in the vicinity of 2-3 and the system was maintained under the same conditions for 15 min. After which, the system was cooled and the product was precipitated by addition of isopropanol, washed with isopropanol:water (80:20 and 90:10) and dried under reduced pressure. The product was characterized by IR and $^1$H-NMR spectroscopy. Reaction yield: 95%, amination with reducing sugar: 20%.

Example 21. Amine Derivatives of Partially Deacetylated Hyaluronic Acid (Reductive Amination with Reducing Sugars)

An aqueous solution of partially deacetylated sodium hyaluronate obtained according to Example 9 (2% w/v) was admixed with lactose (3 eq.) and the pH adjusted with acetic acid (100%) to reach values in the vicinity of 5.5. The system thus obtained was heated to 60° C. and then admixed with a 2-methylpyridine borane solution (1 eq., 10% w/v) in isopropanol and left to react for 3 hours under the same conditions. Subsequently the pH of the reaction was adjusted with aqueous hydrochloric acid (4N) to reach values in the vicinity of 2-3 and the system was maintained under the same conditions for 15 min. After which, the system was cooled, and the product was precipitated by addition of isopropanol, washed with isopropanol:water (80:20 and 90:10) and dried under reduced pressure. The product was characterized by IR and $^1$H-NMR spectroscopy. Reaction yield: 95%, amination with reducing sugar: 15%.

Example 22. Amide Derivatives of Compounds Obtained According to Examples 17-21 (Amidation of Derivatives Obtained Through Reductive Amination of Hyaluronic Acid with Reducing Sugars)

A solution of amine derivative of hyaluronic acid obtained according to Example 17 (0.25% w/v) in water was admixed with the amine derivative obtained in Example 1 (30 eq.) and the resulting solution pH was adjusted to a 6.8 through appropriate addition of sodium hydroxide (1N, 0.1N) or hydrochloric acid (1N, 0.1N). Subsequently, a solution of (3-dimethylaminopropyl)-N'-ethylcarbodiimide hydrochloride (5 eq., 11% w/v) and hydroxybenzotriazole (3.5 eq., 6% w/v) which had been previously solubilized in water:dimethyl sulfoxide (1.1:1) was added drop by drop. The pH of the solution was adjusted to 6.8 through appropriate addition of sodium hydroxide (1N, 0.1N) and the resulting raw product was left to react at room temperature for 16 hours. Subsequently, the pH was appropriately adjusted to 7 with sodium hydroxide/hydrochloric acid (0.1N) and the resulting solution was dialyzed repeatedly (cutoff: 12-14000) against water. After which, the solution was admixed with sodium chloride until a 5% w/v titer was reached and the desired product precipitated with ethanol, dried and characterized by IR and $^1$H-NMR spectroscopy. Reaction yield: 90%, amidation with amine derivative of the reducing sugar: 90%.

Example 23. Amide Derivatives of Partially Deacetylated Hyaluronic Acid (Acylation with Carboxylic Derivatives of Reducing Sugars)

A solution of deacetylated sodium hyaluronate obtained according to Example 7 (0.30% w/v) in water was admixed with lactobionic acid (30 eq.) and the resulting solution pH was adjusted to a 6.8 through appropriate addition of sodium hydroxide (1N, 0.1N) or hydrochloric acid (1N, 0.1N). Subsequently, a solution of (3-dimethylaminopropyl)-N'-ethylcarbodiimide hydrochloride (5 eq., 11% w/v) and hydroxybenzotriazole (3.5 eq., 6% w/v) which had been previously solubilized in water:dimethyl sulfoxide (1.1:1) was added drop by drop. The pH of the solution was adjusted to 6.8 through appropriate addition of sodium hydroxide (1N, 0.1N) and the resulting raw product was left to react at room temperature for 16 hours. Subsequently, the pH was appropriately adjusted to 7 with sodium hydroxide/hydrochloric acid (0.1N) and the resulting solution was dialyzed repeatedly (cutoff: 12-14000) against water. After which, the solution was admixed with sodium chloride until a 5% w/v titer was reached and the desired product precipitated with ethanol, dried and characterized by IR and $^1$H-NMR spectroscopy. Reaction yield: 79%, acylation with lactobionic acid: 5%.

Example 24. Amide Derivatives of Partially Deacetylated Hyaluronic Acid (Acylation with Carboxylic Derivatives of Reducing Sugars)

A solution of lactobionic acid prepared according to Example 4 was added to a solution of deacetylated sodium hyaluronate obtained according to Example 7 (0.5 eq., 0.30% w/v) in water and the raw product thus obtained was left to react at room temperature for 16 hours. Subsequently, the pH was appropriately adjusted to 7 with sodium hydroxide/hydrochloric acid (0.1N) and the resulting solution was dialyzed repeatedly (cutoff: 12-14000) against water. After which, the solution was admixed with sodium chloride until a 5% w/v titer was reached and the desired product precipitated with ethanol, dried and characterized by IR and $^1$H-NMR spectroscopy. Reaction yield: 87%, acylation with lactobionic acid: 16%.

Example 25. Amide Derivatives of Partially Deacetylated Hyaluronic Acid (Acylation with Carboxylic Derivatives of Reducing Sugars)

A solution of lactobionic acid prepared according to Example 4 was added to a solution of deacetylated sodium hyaluronate obtained according to Example 7 (0.5 eq., 30% w/v) in water and the raw product thus obtained was left to react at room temperature for 16 hours. Subsequently, a saturated sodium chloride solution was added in a sufficient amount to obtain a final titer of 5% w/v in sodium chloride, the mixture was left under stirring for 1 hour, and finally the product precipitated by the addition of acetone and the solid obtained was isolated and then dried. The product was characterized by IR and $^1$H-NMR spectroscopy. Reaction yield: 85%, acylation with lactobionic acid: 16%.

Example 26. Amide Derivatives of Partially Deacetylated Hyaluronic Acid (Acylation with Carboxylic Derivatives of Reducing Sugars) in Organic Medium A solution of lactobionic acid prepared according to Example 4 was added to a solution of deacetylated tetrabutylammonium hyaluronate obtained according to Example 11 (0.5 eq., 2% w/v) in dimethyl sulfoxide and the raw product thus obtained was left to react at room temperature for 16 hours. Subsequently, a saturated sodium chloride solution was added in a sufficient amount to obtain a final titer of 5% w/v in sodium chloride, the mixture was left under stirring for 1 hour, and finally the product precipitated by the addition of acetone and the solid obtained was isolated and then dried. The product was characterized by IR and $^1$H-NMR spectroscopy. Reaction yield: 80%, acylation with lactobionic acid: 10%.

Example 27. Amide Derivatives of Partially Deacetylated Hyaluronic Acid (Acylation with Carboxylic Derivatives of Reducing Sugars) in Organic Medium A solution of lactobionic acid prepared according to Example 4 was added to a solution of deacetylated sodium hyaluronate obtained according to Example 7 (0.5 eq., 2% w/v) in dimethylformamide and the raw product thus obtained was left to react at room temperature for 16 hours.

Subsequently, a saturated sodium chloride solution was added in a sufficient amount to obtain a final titer of 5% w/v in sodium chloride, the mixture was left under stirring for 1 hour, and finally the product precipitated by the addition of acetone and the solid obtained was isolated and then dried. The product was characterized by IR and $^1$H-NMR spectroscopy. Reaction yield: 88%, acylation with lactobionic acid: 19%.

Example 28. Amide Derivatives of Compounds Obtained According to Examples 23-27 (Amidation of Derivatives Obtained Through Acylation of Hyaluronic Acid with Amine Derivatives of Reducing Sugars)

A solution of amide derivative of hyaluronic acid obtained according to Example 24 (0.25% w/v) in water was admixed with the amine derivative obtained in Example 1 (30 eq.) and the resulting solution pH was adjusted to a 6.8 through appropriate addition of sodium hydroxide (1N, 0.1N) or hydrochloric acid (1N, 0.1N). Subsequently, a solution of (3-dimethylaminopropyl)-N'-ethylcarbodiimide hydrochloride (5 eq., 11% w/v) and hydroxybenzotriazole (3.5 eq., 6% w/v) which had been previously solubilized in water:dimethyl sulfoxide (1.1:1) was added drop by drop. The pH of the solution was adjusted to 6.8 through appropriate addition of sodium hydroxide (1N, 0.1N) and the resulting raw product was left to react at room temperature for 16 hours. Subsequently, the pH was appropriately adjusted to 7 with sodium hydroxide/hydrochloric acid (0.1N) and the resulting solution was dialyzed repeatedly (cutoff: 12-14000) against water. After which, the solution was admixed with sodium chloride until a 5% w/v titer was reached and the desired product precipitated with ethanol, dried and characterized by IR and $^1$H-NMR spectroscopy. Reaction yield: 84%, amidation with amine derivative of the reducing sugar: 93%.

Example 29. Reduction in Inflammatory Markers

NIH-3T3 line mouse fibroblasts were expanded in DMEM in the presence of 10% foetal calf serum FCS and treated with IL1β 1 ng/ml for 24 hours. Subsequently, some of the cultures were incubated with the amide derivative of hyaluronic acid obtained according to Example 13 with a concentration of 1.25 mg/ml. Cell RNA was extracted at 6, 12, and 24 hours from treatment for subsequent analysis of expression of pro-inflammatory cytokine TGF-β1 by qPCR. Said analysis was performed using RotorGene Q series, which allows gene expression to be quantified during an amplification reaction. In the reaction mixture for qPCR, there is a fluorescent molecule which binds to the minor groove of the double-stranded DNA molecule. For each reaction a negative control was also performed (reaction mixture without cDNA). The experiments were performed in duplicate and the statistical analysis performed by a two-tailed t-test. Differences with a t-test value <0.05 were considered significant. The value stated in the table corresponds to 2^-ΔΔCt, obtained according to relative quantification with the Pfaffl 2^-ΔΔCt method (PfafflM.V. Nucleic Acid Research 2001, 29 (9): e45):

ΔCt=Ct housekeeping−Ct gene target

ΔΔCt=ΔCt sample−ΔCt control

2^-ΔΔCt

| Time (hours) | Untreated control TGF-β1 | Control treated with IL1β TGF-β1 | Treated with IL1β and amide derivative of hyaluronic acid TGF-β1 |
|---|---|---|---|
| 6 | 1.000 | 2.101 | 1.289 |
| 12 | 1.000 | 1.112 | 0.946 |
| 24 | 1.000 | 0.778 | 0.462 |

The ability to regulate pathological processes influenced by galectins is well evidenced by Example 29, where the hyaluronic acid derivatives obtained according to the present invention demonstrate a remarkable ability to reduce expression of TGF-β1, a cytokine downstream of the inflammatory cascade in processes regulated by galectin 3, such as fibrosis.

The invention claimed is:

1. Functionalized hyaluronic acid or a derivative thereof having the formula (I)

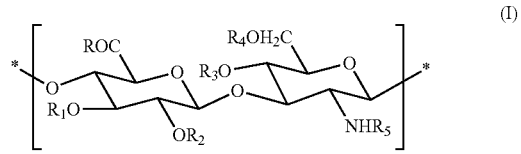

wherein $R_1$, $R_2$, $R_3$, $R_4$ are, independently of one another, H, $SO_3^-$, an acyl group derived from a carboxylic acid of the aliphatic, aromatic, arylaliphatic, cycloaliphatic, heterocyclic series, —CO—$(CH_2)_2$—COOY, where Y is a negative charge or H, and R is Z(1) or Z(2), and $R_5$ is —CO—$CH_3$, H, $SO_3^-$, an acyl group derived from a carboxylic acid of the aliphatic, aromatic, arylaliphatic, cycloaliphatic, heterocyclic series, an acyl group of acid hyaluronic acid, where Z(1) is a moiety of formula (1):

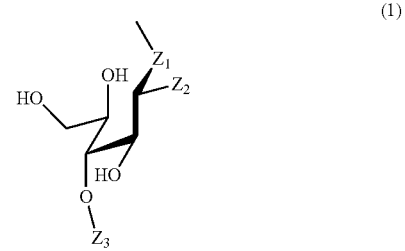

wherein $Z_1$ is —$NR_6CH_2$—, and $R_6$ is H or an aliphatic, aromatic, arylaliphatic, cycloaliphatic, heterocyclic group, substituted or non-substituted, $Z_2$ is —OH, or —NHCOCH$_3$, $Z_3$ is H, monosaccharide, disaccharide, or oligosaccharide, or Z(2) is a moiety of formula (2):

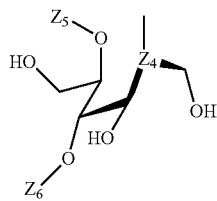

wherein $Z_4$ is —$NR_6CH$—, and $R_6$ is H or an aliphatic, aromatic, arylaliphatic, cycloaliphatic, heterocyclic group, substituted or non-substituted, $Z_5$ and $Z_6$ are, independently of each other, H, monosaccharide, disaccharide, or oligosaccharide, or $R_5$ is Z(3) or Z(4), and R is $NR_6R_7$, or an alcoholic group of the aliphatic, aromatic, arylaliphatic, cycloaliphatic, heterocyclic series, OH, O⁻, an alcoholic group of hyaluronic acid, an amino group of hyaluronic acid, and $R_6$, $R_7$ are, independently of each other, H or an aliphatic, aromatic, arylaliphatic, cycloaliphatic, heterocyclic group, substituted or non-substituted, where Z(3) is a moiety of formula (3):

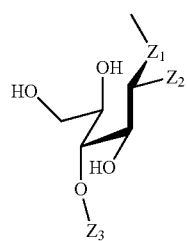

wherein $Z_1$ is —$CH_2$— or —CO—, $Z_2$ is —OH, or —$NHCOCH_3$, $Z_3$ is H, monosaccharide, disaccharide, or oligosaccharide, or Z(4) is a moiety of formula (4):

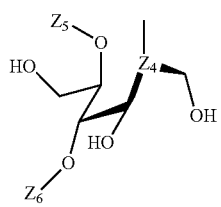

wherein $Z_4$ is —CH—, $Z_5$ and $Z_6$ are, independently of each other, H, monosaccharide, disaccharide, or oligosaccharide, or R is Z(1) or Z(2), and $R_5$ is Z(3) or Z(4).

2. The functionalized hyaluronic acid or a derivative thereof of claim 1, wherein $Z_3$, $Z_5$ and $Z_6$ are, independently of one another, H, moiety of glucose, galactose, arabinose, xylose, mannose, lactose, trealose, gentiobiose, cellobiose, cellotriose, maltose, maltotriose, chitobiose, chitotriose, mannobiose, melibiose, fructose, N-acetyl glucosamine, N-acetyl galactosamine, or a combination thereof.

3. The functionalized hyaluronic acid or a derivative thereof of claim 1, wherein $Z_3$ is H, moiety of glucose, galactose, mannose, N-acetyl glucosamine, N-acetyl galactosamine, or a combination thereof.

4. The functionalized hyaluronic acid or a derivative thereof of claim 1, wherein Z is a moiety of lactose or galactose, where Z is any one of Z(1), Z(2), Z(3) and Z(4).

5. The functionalized hyaluronic acid or a derivative thereof of claim 1 in the form of a biomaterial or scaffold for cell growth.

6. A pharmaceutical composition comprising at least one functionalized hyaluronic acid or a derivative thereof of claim 1, and at least one pharmacologically active substance and/or at least one bioactive substance, wherein:

said pharmacologically active substance is selected from antibiotics, anti-infectives, antimicrobials, antivirals, cytostatic, cytotoxic, antitumor, anti-inflammatory, cicatrizant, anaesthetics, analgesics, vasoconstrictors, cholinergic or adrenergic agonists and antagonists, antithrombotic, anticoagulant, haemostatic, fibrinolytic, thrombolytic, proteins and fragments thereof, peptides, polynucleotides, growth factors, enzymes, vaccines, and combinations thereof, and said bioactive substance is selected from collagen, fibrinogen, fibrin, alginic acid, sodium alginate, potassium alginate, magnesium alginate, cellulose, chondroitin sulfate, dermatan sulfate, keratan sulfate, heparin, eparan sulfate, laminin, fibronectin, elastin, polylactic acid, polyglycolic acid, poly(lactic-co-glycolic acid), polycaprolactone, gelatin, albumin, poly(glycolide-co-caprolactone), poly(glycolide-co-trimethylene carbonate), hydroxyapatite, tricalcium phosphate, dicalcium phosphate, demineralized bone matrix, and mixtures thereof.

7. A method for treating pathologies ascribable to an altered expression of galectins, said pathologies comprising non-alcoholic steatohepatitis, plaque psoriasis, rheumatoid arthritis, osteoarthritis, neoplasia, and pulmonary, renal, and cardiovascular fibrotic processes, wherein said method comprises the step of administering to patients in need thereof a therapeutically effective amount of the functionalized hyaluronic acid or a derivative thereof of claim 1 or the pharmaceutical composition of claim 6.

8. The functionalized hyaluronic acid or a derivative thereof of claim 1, wherein said derivative of hyaluronic acid is a moiety of:

a hyaluronic acid salt, selected from sodium hyaluronate, potassium hyaluronate, calcium hyaluronate, magnesium hyaluronate, zinc hyaluronate, cobalt hyaluronate, ammonia hyaluronate, tetrabutylammonium hyaluronate, and mixtures thereof, a hyaluronic acid ester, wherein a part or all of the carboxylic groups are esterified with aliphatic, aromatic, arylaliphatic, cycloaliphatic, or heterocyclic series alcohols, a self-cross-linked hyaluronic acid ester, wherein a part or all of the carboxylic groups are esterified with alcoholic groups from the same polysaccharide chain or other chains, a cross-linked hyaluronic acid compound, wherein a part or all of the carboxylic groups are esterified with aliphatic, aromatic, arylaliphatic, cycloaliphatic, or heterocyclic series polyalcohols, generating cross-linking by spacer chains, a succinic acid hemiester or succinic acid heavy metal salt with hyaluronic acid or with partial or total hyaluronic acid esters,
an O-sulfated derivative, or a N-sulfated derivative.

* * * * *